United States Patent
Spoof

(10) Patent No.: US 11,166,648 B2
(45) Date of Patent: Nov. 9, 2021

(54) METHOD AND SYSTEM FOR ESTIMATING PATIENT RECOVERY TIME UTILIZING NEUROMUSCULAR TRANSMISSION MEASUREMENTS

(71) Applicant: General Electric Company, Schenectady, NY (US)

(72) Inventor: Markku Erik Spoof, Helsinki (FI)

(73) Assignee: General Electric Company, Schenectady, NY (US)

( * ) Notice: Subject to any disclaimer, the term of this patent is extended or adjusted under 35 U.S.C. 154(b) by 673 days.

(21) Appl. No.: 15/988,176

(22) Filed: May 24, 2018

(65) Prior Publication Data

US 2019/0357810 A1 Nov. 28, 2019

(51) Int. Cl.
*A61B 5/11* (2006.01)
*A61B 5/00* (2006.01)
*A61B 5/389* (2021.01)

(52) U.S. Cl.
CPC .......... *A61B 5/1106* (2013.01); *A61B 5/4519* (2013.01); *A61B 5/389* (2021.01); *A61B 5/4821* (2013.01); *A61B 5/7217* (2013.01); *A61B 5/7225* (2013.01); *A61B 2505/05* (2013.01)

(58) Field of Classification Search
CPC ... A61B 5/1106; A61B 5/4519; A61B 5/4821; A61B 5/0488
See application file for complete search history.

(56) References Cited

U.S. PATENT DOCUMENTS

| | | | |
|---|---|---|---|
| 4,387,723 A * | 6/1983 | Atlee, III | A61B 5/1106 600/547 |
| 4,595,018 A | 6/1986 | Rantala | |
| 5,697,381 A | 12/1997 | Rantala et al. | |
| 5,851,191 A * | 12/1998 | Gozani | A61B 5/0488 600/554 |
| 6,389,312 B1 * | 5/2002 | Duckert | A61B 5/1106 600/546 |
| 7,496,400 B2 | 2/2009 | Hoskonen et al. | |
| 2002/0095098 A1 * | 7/2002 | Marinello | A61B 5/0484 600/544 |

(Continued)

OTHER PUBLICATIONS

International Search Report and Written Opinion dated Sep. 12, 2019, PCT application # PCT/US2019/033742 filed May 23, 2019; 15 pages.

(Continued)

*Primary Examiner* — Sean P Dougherty
(74) *Attorney, Agent, or Firm* — Andrus Intellectual Property Law, LLP

(57) ABSTRACT

Method and systems are provided for monitoring neuromuscular blockade in patients during surgical procedures. The system and method utilizes a stimulator to provide stimulation to a nerve of the patient, such as train-of-four (TOF). Following such stimulation, the system and method monitors for muscle twitch reaction and, based upon the monitored muscle twitches, the system and method creates a neuromuscular blocking trend curve. The neuromuscular blocking trend curve provides an estimated time of recovery for the patient and provides the estimated recovery time to a clinician. The estimated recovery time allows the clinician to modify treatment of the patient to accelerate recovery if required.

20 Claims, 10 Drawing Sheets

(56) References Cited

U.S. PATENT DOCUMENTS

| | | | |
|---|---|---|---|
| 2003/0055355 A1* | 3/2003 | Viertio-Oja | A61B 5/0476 600/544 |
| 2003/0167019 A1* | 9/2003 | Viertio-Oja | A61B 5/4821 600/544 |
| 2005/0283204 A1 | 12/2005 | Buhlmann | |
| 2010/0081963 A1* | 4/2010 | Gilhuly | A61B 5/746 600/554 |
| 2013/0204155 A1* | 8/2013 | Brull | A61B 5/1106 600/546 |
| 2013/0204156 A1* | 8/2013 | Hampton | A61B 5/4052 600/546 |
| 2014/0107524 A1* | 4/2014 | Brull | A61B 5/389 600/554 |
| 2014/0235991 A1* | 8/2014 | Gadsby | A61B 5/04001 600/391 |
| 2015/0032022 A1 | 1/2015 | Stone | |
| 2018/0333569 A1* | 11/2018 | Snow | A61B 5/0488 |
| 2019/0008453 A1* | 1/2019 | Spoof | A61B 5/4848 |
| 2019/0192051 A1* | 6/2019 | Savinen | A61B 5/486 |
| 2019/0223764 A1* | 7/2019 | Hulvershorn | A61B 5/7217 |

OTHER PUBLICATIONS

"Neuromuscular Transmission". GE Healthcare Quick Guide. Jan. 2017.

Unpublished U.S. Appl. No. 15/646,005, filed Jul. 10, 2017, entitled "Method and System for Neuromuscular Transmission Measurement".

* cited by examiner

METHOD AND SYSTEM FOR ESTIMATING PATIENT RECOVERY TIME UTILIZING NEUROMUSCULAR TRANSMISSION MEASUREMENTS

FIELD

The present disclosure relates to medical devices, and more particularly, to medical devices and methods of operating medical devices for monitoring neuromuscular transmission during a surgical procedure.

BACKGROUND

Neuro Muscular Transmission (NMT) is the transfer of an impulse between a nerve and a muscle in the neuromuscular junction. NMT may be blocked in a patient undergoing a surgical procedure, for example, by neuromuscular blocking agents/drugs, which may cause transient muscle paralysis and prevent the patient from moving and breathing spontaneously.

Muscle relaxation is used during general anesthesia to enable endotracheal intubation and to provide the surgeon with optimal working conditions. At the end of a surgical procedure, the level of NMT is used to determine when the patient can be extubated. Thus, the level of neuromuscular block may be monitored to ensure appropriate block is provided for the given procedure and to determine when the patient can be safely extubated.

SUMMARY

In one embodiment, a method to estimate recover time of a patient from a neuromuscular block includes applying a first TOF stimulation to a nerve of the patient at a first measurement time. First, second, third and fourth muscle twitches are measured in response to the first TOF stimulation. A second TOF stimulation is applied to the nerve of the patient at a second measurement time and the muscle twitches in response to the second TOF stimulation are measured. Based upon the muscle twitches in response to the first and second TOF stimulations, the method calculates an estimated recovery time and the estimated recovery time is provided to a clinician.

In one embodiment, the estimated recovery time is calculated by creating a predicted neuromuscular blocking trend curve. The predicted neuromuscular blocking trend curve extrapolates from the measured TOF ratios to estimate the recovery time when the TOF ratio will exceed a predefined level. The predicted neuromuscular blocking trend curve can be calculated utilizing different algorithms that involve either measured parameters from the patient or are based upon historic patient trends. In either case, the predicted neuromuscular blocking trend curve presents an estimated recovery time at which the intubation tube can be removed from the patient and the patient can breathe spontaneously.

In another embodiment, a medical device for multi-parameter monitoring of a patient includes a stimulator to apply train-of-four stimulation to a nerve of the patient. An electromyography (EMG) sensor or other type of sensor detects first, second, third and fourth muscle twitches in response to the TOF stimulation. A controller is operable to create a predicted neuromuscular blocking trend curve that is based upon the detected muscle twitches as well as other parameters, such as historic patient trends. The medical device includes a display that visually displays the predicted neuromuscular blocking trend curve along with measured TOF ratios and predicted TOF ratios. The controller monitors the measured TOF ratios relative to the predicted TOF ratios and adjusts the predicted neuromuscular blocking trend curve as needed.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of a neuromuscular transmission (NMT) monitoring system configured to monitor an amount of neuromuscular blockage after the administration of muscle relaxants in patients during surgery. Neuro Muscular Transmission (NMT) is the transfer of an impulse between a nerve and a muscle in the neuromuscular junction. NMT may be blocked by neuromuscular blocking agents/drugs, which may cause transient muscle paralysis and prevent the patient from moving and breathing spontaneously. Additionally, muscle relaxation may be used during general anesthesia to enable endotracheal intubation and to provide the surgeon with optimal working conditions. At the end of a surgical procedure, the neuromuscular block is reversed such that neuromuscular activity may be returned to normal and that the patient may be able to breathe unassisted, before the removal of the endotracheal intubation (i.e. extubation). Thus, appropriate assessment of the degree of NMT block may be used for ensuring proper timing of intubation and for guiding intraoperative administration of neuromuscular blocking agents, maintaining a desired degree of intraoperative neuromuscular block, and ultimately preventing the occurrence of residual muscle paralysis.

An NMT monitor may be used to monitor muscle response to electrical stimulation of a motor nerve (e.g., ulnar nerve). For example, an electrical stimulus may be provided at the ulnar nerve near the wrist and the response of the muscle near the thumb, adductor pollicis, may be monitored. In clinical settings, a nerve stimulator is attached to on top of a motor nerve of the patient and an electrical stimulation current is applied to the patient before induction of anesthesia. A reference value for the muscle response is recorded by the NMT monitor and used to normalize the muscle response once the muscle relaxant is administered. The evoked muscle responses may then be monitored through the measurement of electrical response of the muscle (electromyography (EMG)). In EMG, multiple electrodes may be used to record the compound muscle potential stimulated by the stimulus generator.

According to embodiments disclosed herein, neuromuscular transmission monitoring may be performed by measuring the electrical potentials at the muscle via an electromyography (EMG) sensor, in response to an electric stimulation of a motor nerve.

Figure 1:
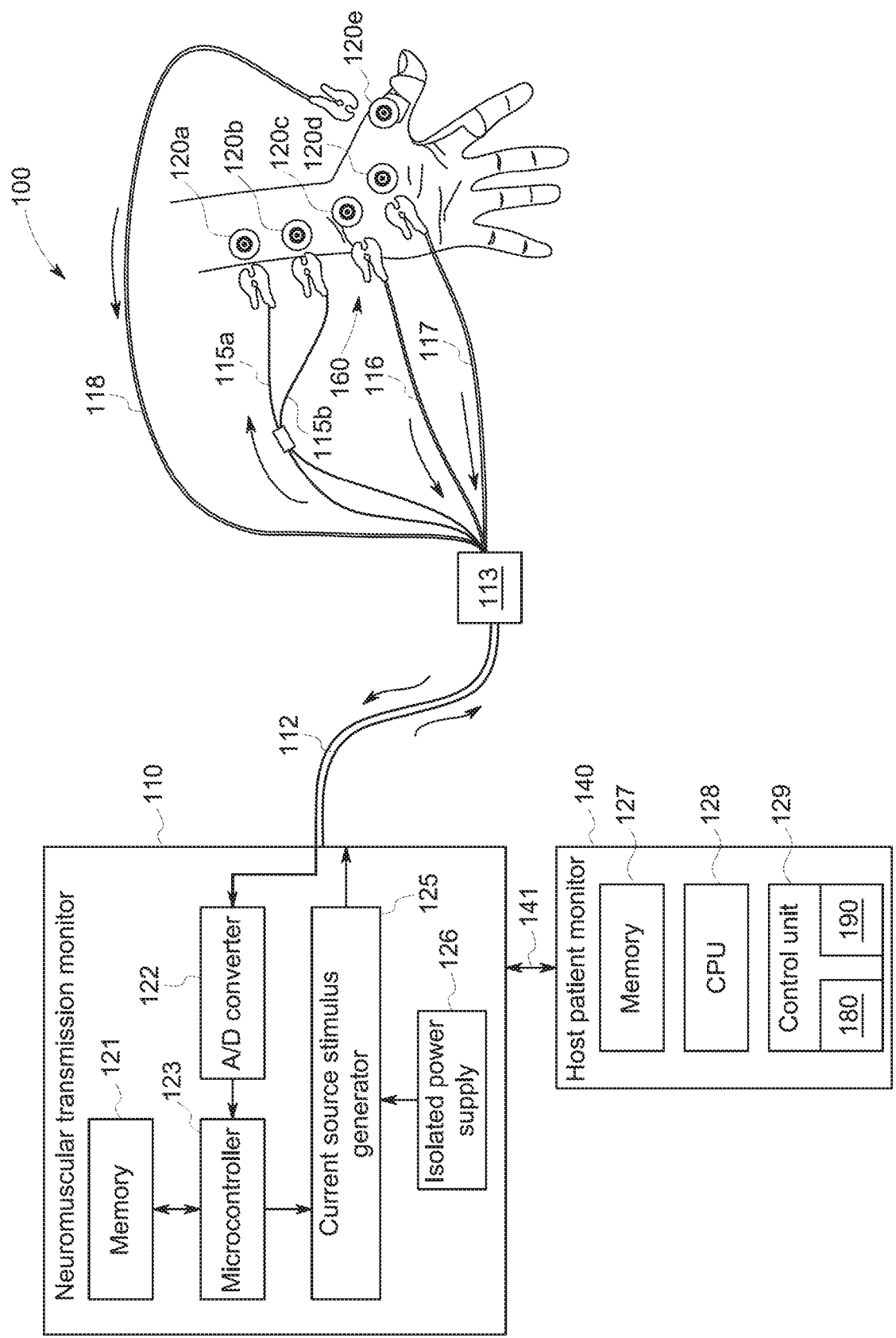
FIG. 1 shows an example neuromuscular transmission monitoring system.

An example of a neuromuscular transmission monitoring system is provided in FIG. 1. The NMT monitoring system may include one or more electro-sensors which detect electrical activity of a muscle (referred to as an EMG sensor) in response to nerve stimulation, and a nerve stimulator. The NMT monitoring system of FIG. 1 also includes a computing system including instructions to carry out one or more control routines for determining a muscle response baseline as well as monitoring neuromuscular block in patients during surgery and post surgery during recovery.

FIG. 1 illustrates an example neuromuscular transmission (NMT) monitoring system 100 that is configured to monitor neuromuscular activity via EMG techniques. NMT monitoring system 100 includes a neuromuscular transmission monitor 110 which is communicatively coupled to a host patient monitor 140 via a communication link 141. The neuromuscular transmission monitor 110 includes a plurality of neurostimulators, 115a and 115b, for providing stimulation output (e.g., electrical stimuli) of varying type and frequency to the patient and at least one input connected to one or more transducers for monitoring the evoked muscle response in response to the electrical stimuli provided by the neurostimulators. The transducers include an EMG sensor 160 consisting of a plurality of electro-sensors for measuring the action potential of muscle contraction in response to nerve stimulation. The signals detected by the transducers may then be converted into electrical signals by the A/D converter 122 of neuromuscular transmission monitor 110.

In the depicted example, neurostimulators 115a and 115b are connected to stimulating electrodes 120a and 120b, respectively, which may apply an electrical stimulus to the patient's ulnar nerve at a pre-determined time interval. The amount of electrical stimulation provided to the neurostimulators is controlled by a current stimulus generator which receives command signals from microcontroller 123. Microcontroller 123 is linked to the user interface of control unit 129, which comprises of a display unit 190 and buttons/knobs 180. The type and frequency of the stimulation output may be adjusted manually by the user (manual mode) or be automatically chosen by the system (automatic mode). In one example, the type and frequency of the stimulation output may be adjusted by the user via pressing buttons or knobs 180 on the patient host monitor 140. In one example, neurostimulators 115a and 115b may be two wires of positive and negative charges, which may be attached by alligator clips to stimulating electrodes 120a and 120b on the skin of the patient's forearm.

A power supply (not shown) may supply electricity to an isolated power supply 126 which in turn provides power to current source stimulus generator 125. The microcontroller 123 may be connected to the current source stimulus generator 125 to adjust the amount of electric current provided to the neurostimulators 115a-b. The current stimulus generator 125 may generate different types of neurostimulation including train-of-four (TOF), single twitch (ST), double burst (DBS), post tetanic count (PTC), current range (e.g., 1-70 mA with 1 mA steps), pulse width/frequency (e.g., 100, 200, 300 µs, or 1 Hz, 2 Hz, etc.). Further, the types of neurostimulation may be chosen via a manual or an automatic stimulating mode. If a manual stimulating mode is chosen, then the user may input the desired neuromuscular stimulating types, current range, and pulse width and/or frequency via pressing button 180 of the host patient monitor 140, for example. Alternatively, if a touch-screen is used as the display unit (e.g., display unit 190 of host patient monitor 140), then user input may be provided via touch input to the touch-screen on the display unit.

If an automatic neurostimulation mode is chosen, microcontroller 123 of neuromuscular transmission monitor 110 may select a first neurostimulation type as its default setting, such as TOF stimulation, and based on the muscle response signals received from the EMG sensors, the microcontroller reports the muscle response signals to the user by displaying graphs and numbers (e.g., via display unit 190 of host patient monitor 140). The display unit 190 may display the muscle response data/information to the user and may also include alarm signals/message for alerting the user of potential sensor error.

Additionally, neuromuscular transmission monitor 110 may be connected to a host patient monitor 140 through a communication link 141. Host patient monitor 140 may include memory 127, CPU 128, and control unit 129. Memory 127 may have similar functions as memory 121. Control unit 129 may include control buttons/knobs 180 and display unit 190. The control buttons and knobs of control unit 129 may be configured to allow for user input. The display unit 190 may be configured to receive touch input from a user.

The preferred neuromuscular stimulating output of the present disclosure is a train-of-four (TOF). In one example, TOF may typically use four brief (between 100 and 300 µs) current pulses (generally less than 70 mA) at 2 Hz, repeated every 10 to 20 s as electrostimulation. The resulting twitches (i.e. muscle response) may be measured and quantified for electromyographic response via the EMG sensor. The first twitch (referred to as the T1 twitch) and the last twitch (referred to as the T4 twitch) are compared and the ratio of the last twitch to the first twitch (referred to as TOF ratio) may provide an estimate of the level of neuromuscular blockade (e.g., depth of relaxation) experienced by the patient. The TOF ratio may range from 0 to 100%, for example. The electrical TOF stimuli series may be spaced by ten or more seconds (generally 20 s is used to provide a margin of safety) to give a rest period for full restoration of steady state conditions, as faster stimulation results in smaller evoked responses. TOF stimulation is the most commonly used technique for monitoring the neuromuscular blockade in lightly-blocked patients as well in patients that are recovering from neuromuscular block.

In addition to the TOF ratio, another ratio that can be calculated during TOF stimulation is referred to as TO2.

TO2 is the ratio of the second twitch (T2) to the first twitch (T1) in the train-of-four stimulation pulses.

EMG sensor 160 may include a plurality of electro-sensing connections 116, 117, and 118 connected to sensing electrodes 120c, 120d, and 120e, respectively. Most commonly, the three sensing electrodes are positioned to give the most consistent EMG signals. In the depicted example, sensing electrode 120e is placed over the muscle tendon or finger, sensing electrode 120d is placed over the mid-portion of the muscle close to the neuromuscular junction, while sensing electrode 120c may be variable. In one example, electrodes 120d and 120e may be recording electrodes, while electrode 120c may be a grounding electrode. The grounding electrode provides a common reference for the EMG recording electrodes. For example, the recording electrode 120d may be placed on top of m. adductor pollicis in the thenar eminence and recording electrode 120e may be placed on top of the distal interphalangeal joint of the thumb, while the grounding electrode 120c may be placed at centerline over the flexor retinaculum at the palmar side of the wrist. EMG sensor 160 measures the magnitude of electrical activity sensed by electrodes 120c-120e in response to nerve stimulation and when received at the neuromuscular transmission monitor, is recorded as the EMG muscle response signal.

Stimulating electrodes 120a-120b and sensing electrodes 120c-120e may have mechanisms for improving electrical contact to skin such as ultrasound gel and mechanisms for improving fixation to the skin such as biocompatible adhesives placed beneath the electrodes. Further, the electrodes may be suitable electrodes, such as silver/silver chloride electrodes. Further, the electrodes may be disposable electrodes which can be discarded after a single use. In another example, the stimulators (e.g., stimulators 115a and 115b) and the sensing connections (e.g. electro-sensing connections 116-118, and mechano-sensing connection 114) along with their respective electrodes may be incorporated into a disposable sensing unit. In one example, the disposable sensing unit may be included as part of a one-size-fits-all stretchable glove which may be discarded after a single use.

Further, information regarding the EMG muscle response signals received from EMG sensor 160 may be sent to neuromuscular transmission monitor 110 via main connector 113 and cable 112. In one example, muscle response signals from EMG sensor 160 sensor are fed into a signal scaling and filtering circuit (not shown). After scaling the signal and filtering noise, the signal may be converted from an analog signal to a digital signal in analog-to-digital (A/D) converter 122 and sent to a microcontroller 123 for processing. Further, the muscle response signals may also be amplified via an amplifier (not shown) before being transmitted into the A/D converter 122. The microcontroller 123, or processing unit, is connected to a memory 121 and once the signals are processed, the signal data may be displayed on the display unit 190 of the host patient monitor. In one example, the processed signals may be transmitted to the host patient monitor 140 and displayed on the display unit 190 in real-time. Further still, the processed signals may be updated and stored in memory 121. Memory 121 may be a conventional microcomputer which includes: a central processing unit (CPU), a read-only memory (ROM), a random access memory (RAM), and a conventional data bus. Additionally, the memory may include an automatic calibration module to determine the optimum supramaximal current to provide to the patient based on the muscle response value received by the EMG sensors, and based on the raw signals received from sensors, the module may determine a value, which may be used as a reference value for the neuromuscular blockade monitoring in patient. Further, the automatic calibration module may only be performed when patient is not in paralyzed state. In other words, the automatic calibration module may utilize a reference value based on the signals received from the sensors when patient is in non-relaxed state (e.g., before the administration of the muscle relaxant).

Control unit 129 may also include a user interface (not shown) which can be used to control operation of the NMT monitoring system 100, including controlling the input of patient data, changing the monitoring parameters (e.g. stimulus type, current range, frequency/pulse width, etc.), and the like. The user interface may also include a graphical user interface configured for display on a display device, such as display unit 190. The graphical user interface may include information to be output to a user (such as muscle response signals, patient data, etc.) and may also include menus or other elements through which a user may enter input the control unit 129.

As discussed above, during neuromuscular stimulating of a patient to determine the depth of relaxation, train-of-four (TOF) stimulation is applied to the patient and the muscle response signals are received from EMG sensors for each of the four pulses of the stimulation. The TOF stimulation is applied to the patient at regular intervals, such as every 10-20 seconds and the resulting twitches (i.e. muscle responses) are measured and quantified for electromyographic response by the EMG sensor 160.

Figure 2:
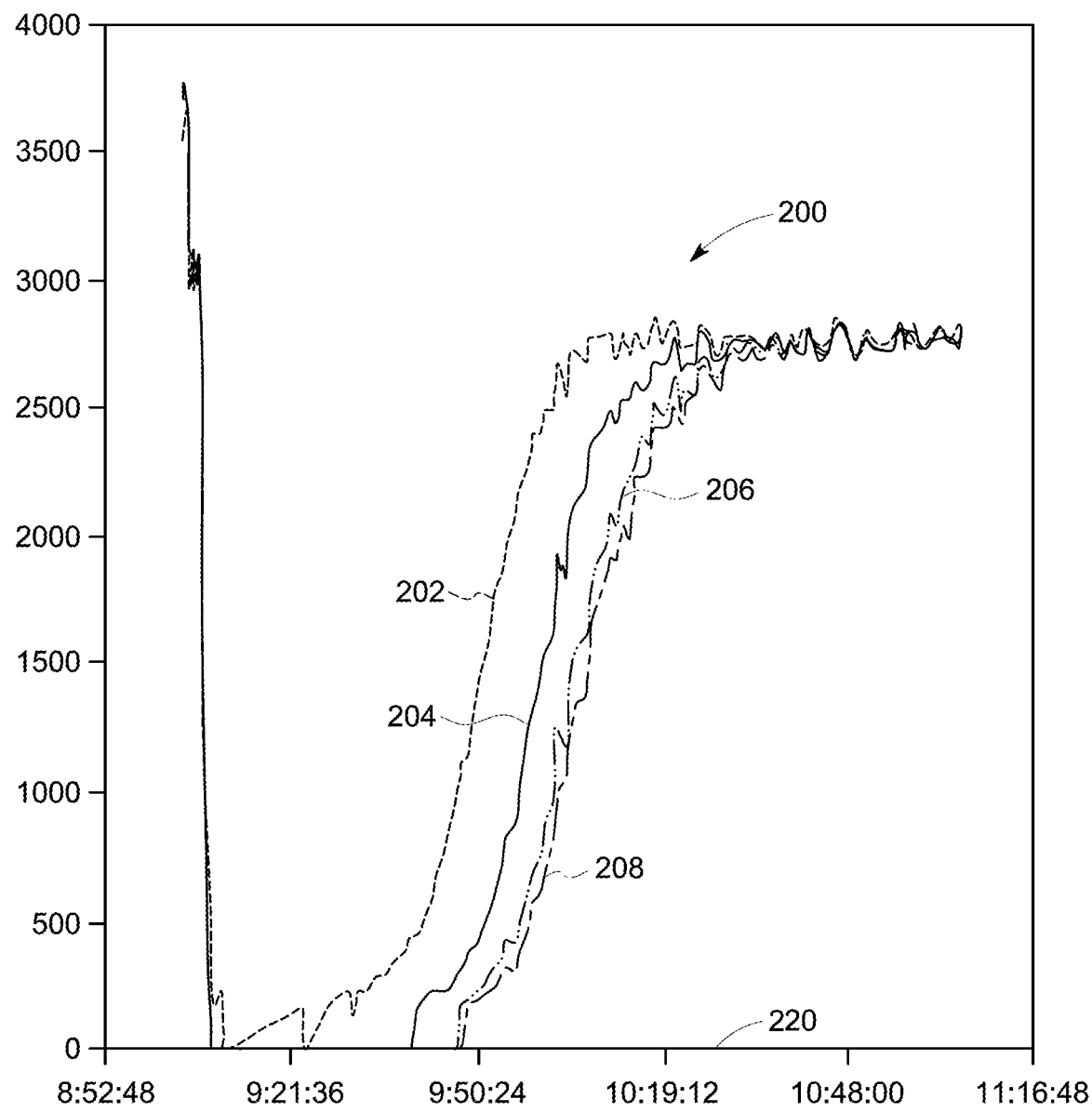
FIG. 2 is a graph showing the muscle twitch responses to a train-of-four (TOF) stimulation over time.

FIG. 2 illustrates the EMG responses to each of the four pulses of a TOF stimulation over a measurement period set forth on the horizontal axis of the graph. The first twitch, referred to as the T1 twitch, is graphically illustrated by trace 202 in the graph 200. The second twitch, referred to as the T2 twitch, is shown by trace 204 while the third twitch, T3, is illustrated by trace 206. The last and final twitch, referred to as the T4 twitch, is shown by trace 208. As can be seen by the combined graph 200 of FIG. 2, the T1 trace 202 begins to be detected at the earliest point in time since the T1 twitch is in response to the first stimulation of the TOF stimulation sequence. The T2, T3 and T4 twitches begin to be detected at a time slightly delayed from the detection of the T1 twitch, as is well known for a the patient recovering from the neuromuscular blocking agent.

In well-known recovery monitoring methods, extubation of the patient should only occur when the recovery of the patient reaches a recovery threshold at which the neuromuscular blocking has been diminished enough to insure proper spontaneous breathing by the patient. In the present disclosure and many monitory systems, the recovery threshold is based upon the ratio of the T4 twitch to the T1 twitch (T4/T1), which is commonly referred to the TOF ratio or TOF %. As described previously, the TOF ratio may range between 0 and 100%. Typically, when the TOF ratio reaches 90%, extubation of the patient is considered to be safe. Thus, the relationship between the T1 twitch and the T4 twitch is very important in determining when the patient can be safely extubated. As can be understood with respect to FIG. 2, the TOF ratio of 90% occurs when the T4 trace 208 begins to closely correspond to the T1 trace 202.

During currently available relaxation depth monitoring utilizing TOF stimulation, a clinician must continue to monitor the patient and wait for the TOF ratio to reach 90% or higher before removing the intubation tube. Although this type of monitoring has proven effective, it requires the clinician to continuously monitor the patient and wait for the TOF ratio to reach the desired value. This requires the clinician to sometimes wait for quite long time (20 minutes or more) while monitoring the TOF ratio. There does not exist an effective way to estimate the recovery time when the TOF ratio will reach and/or exceed the threshold value.

Figure 3:
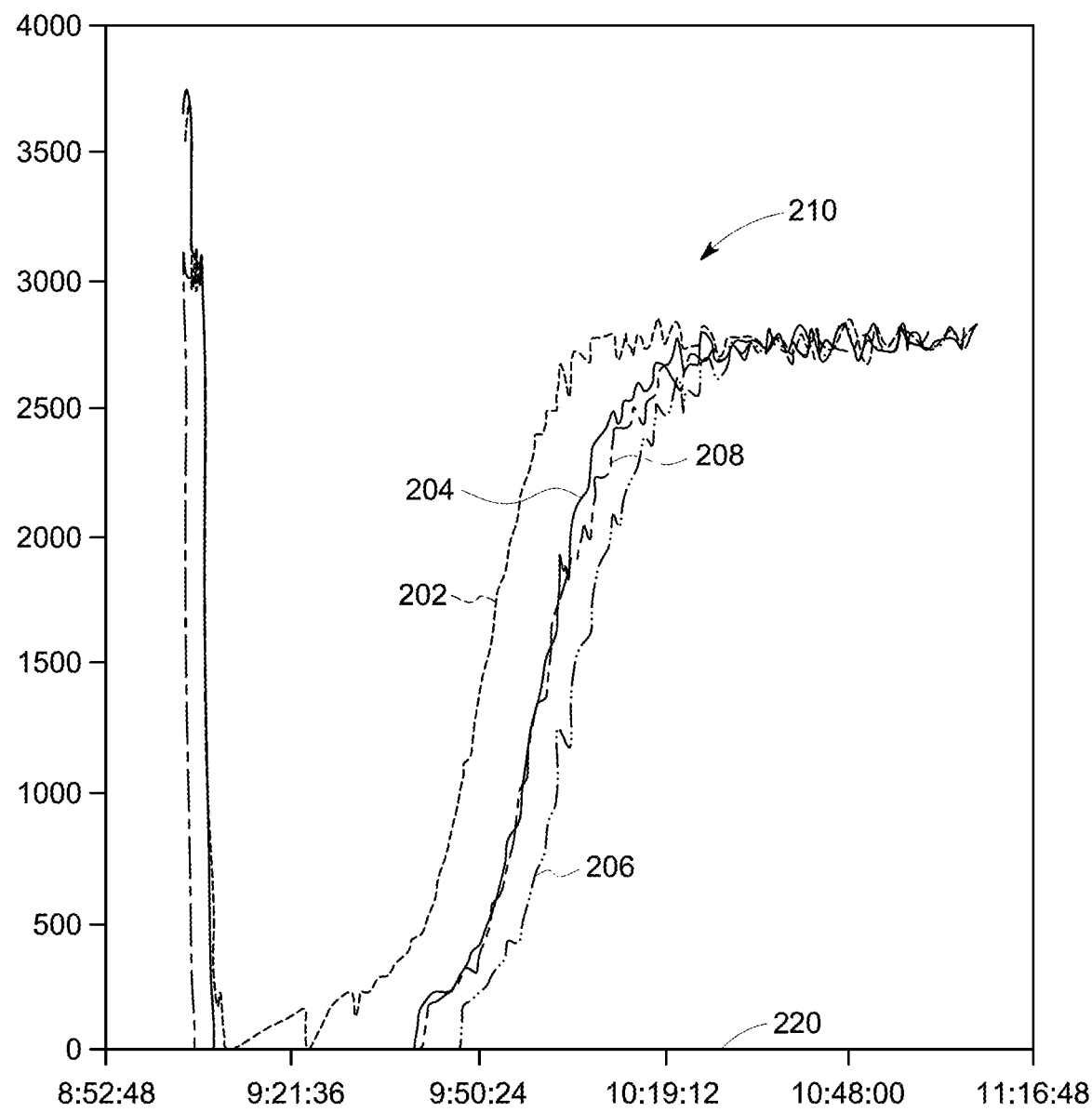
FIG. 3 is a graph showing the muscle twitch response twitches with T4 moved on top of T2.
Figure 4:
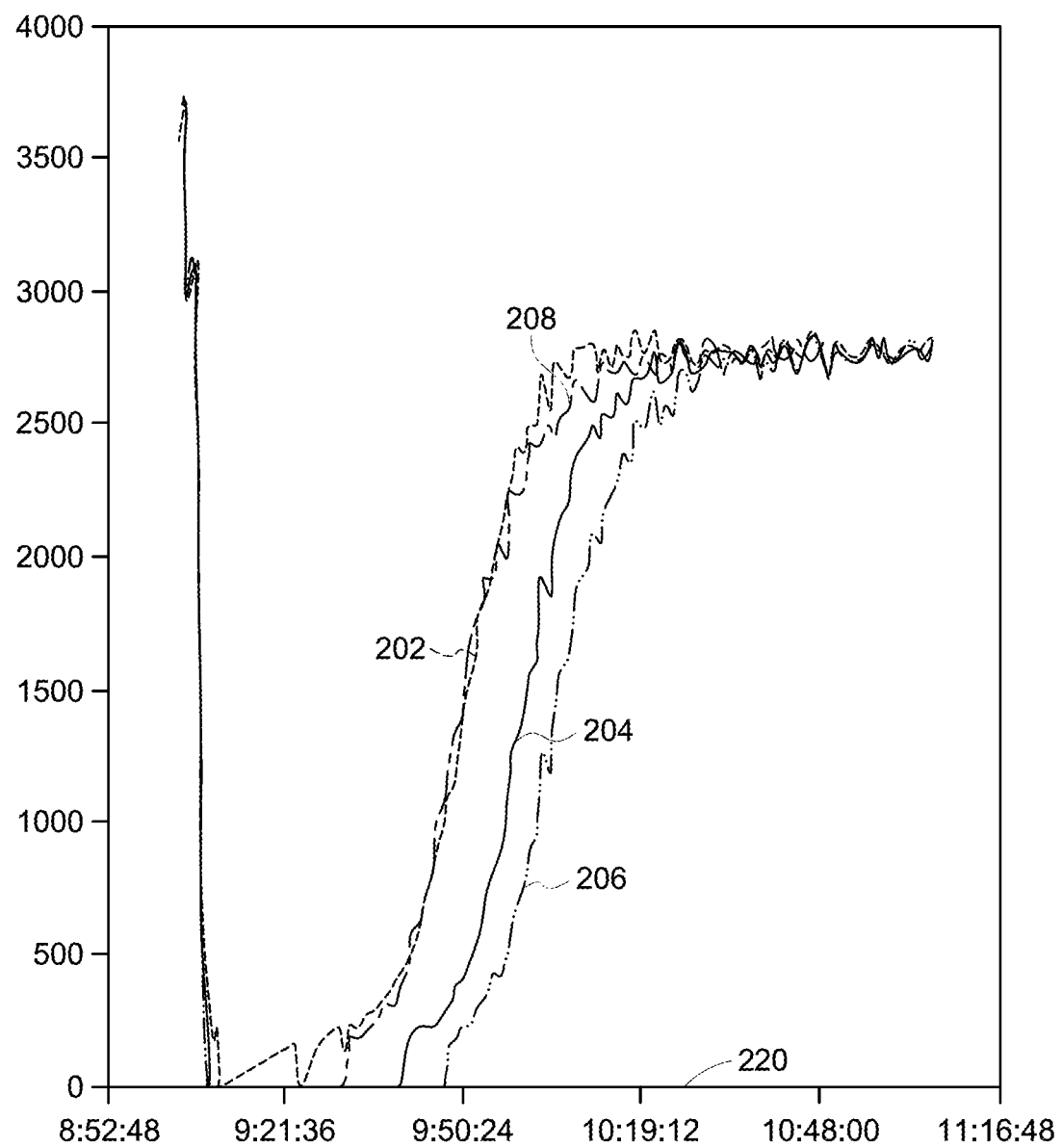
FIG. 4 is a graph showing the muscle twitch response twitches with T4 moved on top of T1.

Referring now to FIG. 3, graph 210 illustrates the similarity in shape between the T2 trace 204 and the T4 trace 208 by superimposing the T4 trace 208 onto the T2 trace 204. Thus, the inventor has recognized that the shape of each of the traces 202, 204, 206 and 208 are similar in shape and are only delayed along the time axis 220. Since the T1 trace occurs sooner than the T4 trace when monitoring the patient, the inventor has recognized that the shape of the T1 and T2 traces can be used to predict the shape of the T4 trace and can be used as an estimate for determining when the TOF ratio will reach the 90% threshold. FIG. 4 provides further evidence that the T4 trace 208 closely matches the T1 trace 202, which is evidenced by superimposing the T4 trace 208 onto the T1 trace 202.

Figure 5:
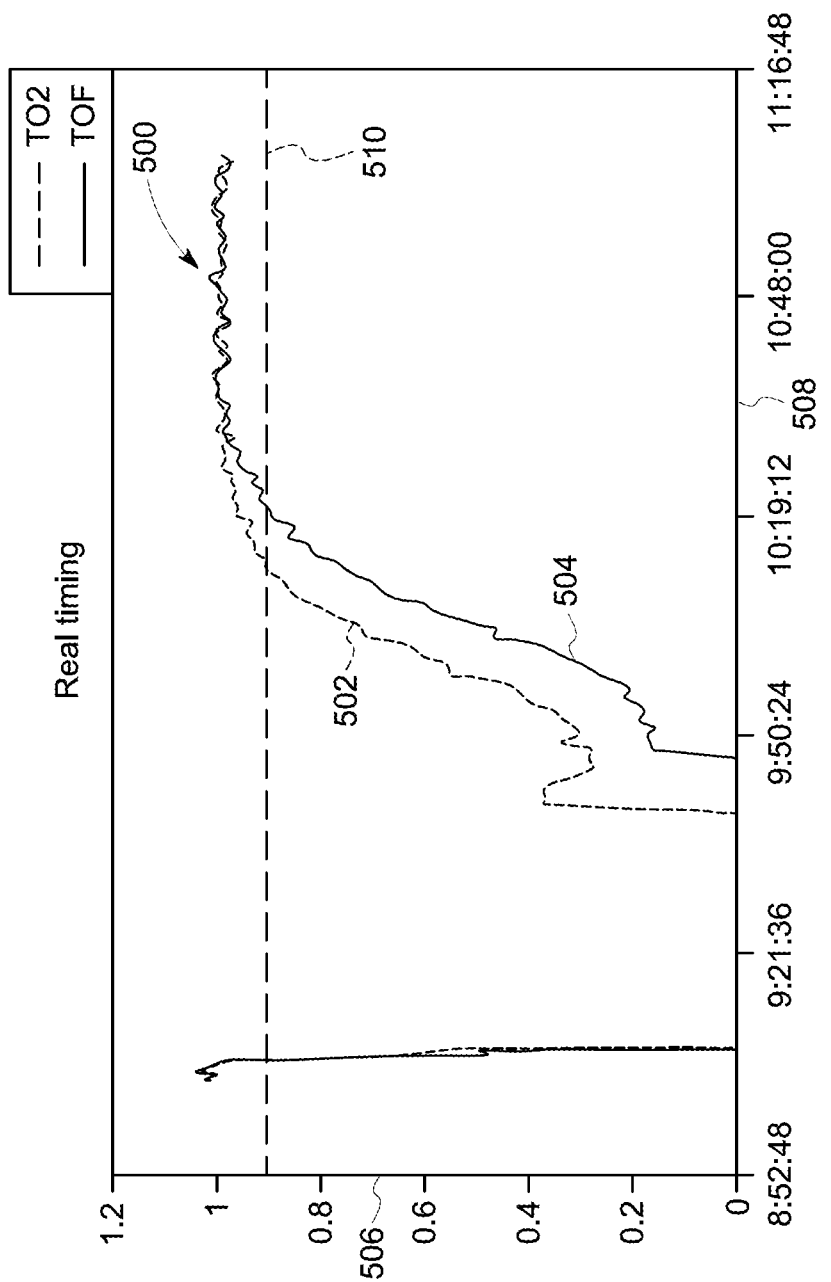
FIG. 5 is a graph showing the TO2 and TOF ratios over time.
Figure 6:
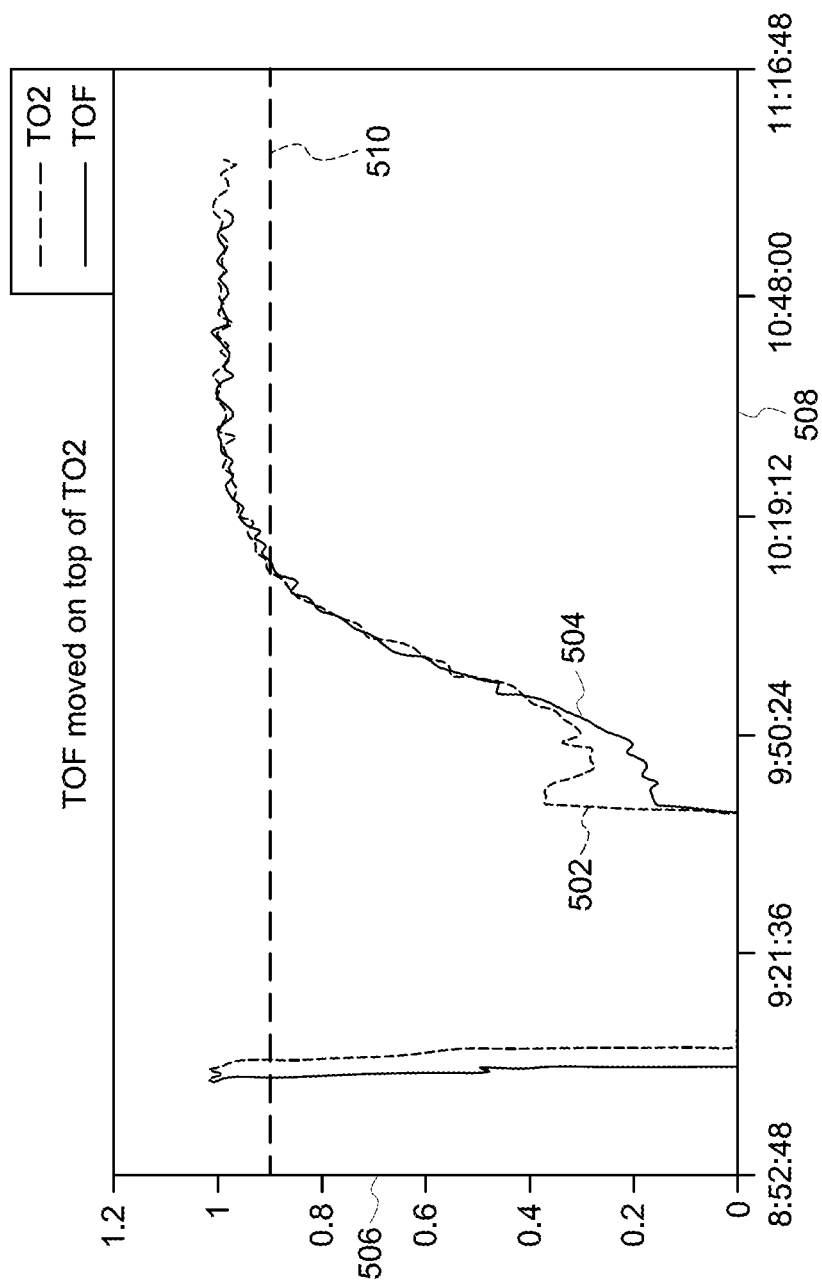
FIG. 6 is a graph similar to FIG. 5 in which the TOF trend is moved on top of the TO2 trend.

Referring now to FIG. 5, graph 500 illustrates two separate ratios that are calculated from a representative patient. The first ratio, which is referred to as the TO2 ratio, represents the ratio of the T2 trace to the T1 trace (T2/T1) and is shown by trend 502. The second trend 504 shown in FIG. 5 is the TOF ratio, which is the T4 twitch relative to the T1 twitch (T4/T1). In the graph 500 of FIG. 5, the vertical axis 506 is a ratio while the horizontal axis 508 is a time axis. As previously discussed, extubation of the patient typically occurs when the TOF ratio, represented by trend 504, exceeds a threshold 510, which in the embodiment of FIG. 5 is 90%. In the embodiment shown, the TOF ratio exceeds the threshold 510 at approximately 10:19. FIG. 6 is a graphic illustration of the correspondence in shape of the TOF ratio trend 504 to the TO2 ratio trend 502. The graphic representation shown in FIG. 6 illustrates that the TO2 trend can be used as an early representative estimate for the TOF trend, which will allow for a prediction of the time when the TOF trend 504 will exceed the threshold 510.

In accordance with the present disclosure, the microcontroller 123 shown in FIG. 1 is configured to provide an estimated recovery time for the patient, which represents a time in the future when the TOF ratio will exceed the extubation threshold, which is typically 90%. The estimated recovery time calculated by the microcontroller 123 can be displayed to the clinician through a display such that the clinician can make treatment decisions, such as either to allow the patient to recover as is occurring or the clinician can decide if an antidote is needed to accelerate the recovery process.

Figure 7A:
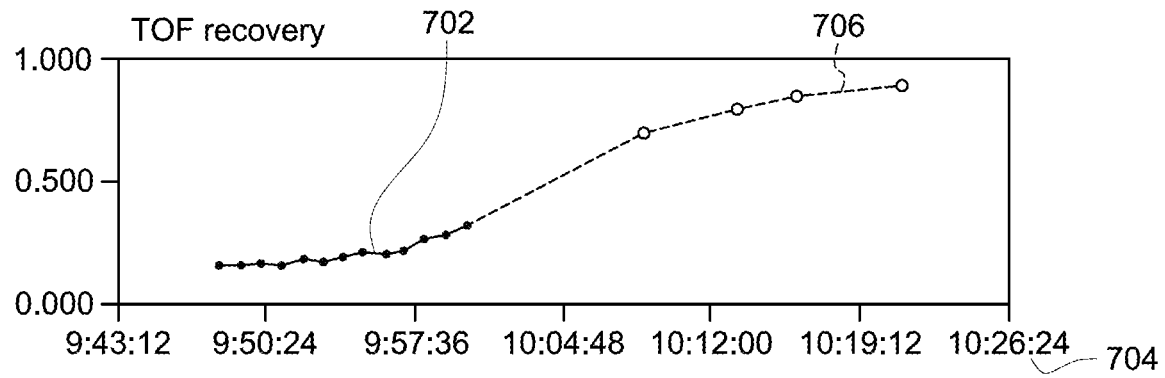
FIGS. 7A-7H are a series of graphs showing the display of measured TOF ratios relative to a predicted neuromuscular blocking trend curve over time.
Figure 7B:
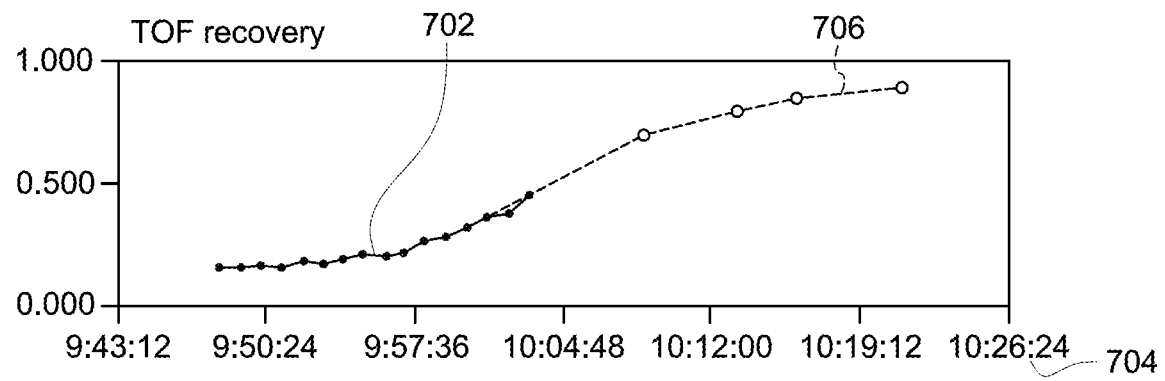
Figure 7C:
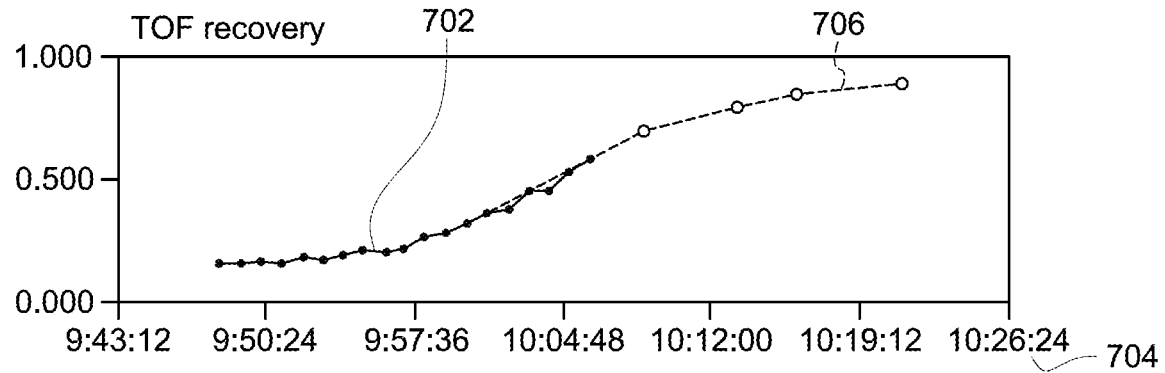
Figure 7D:
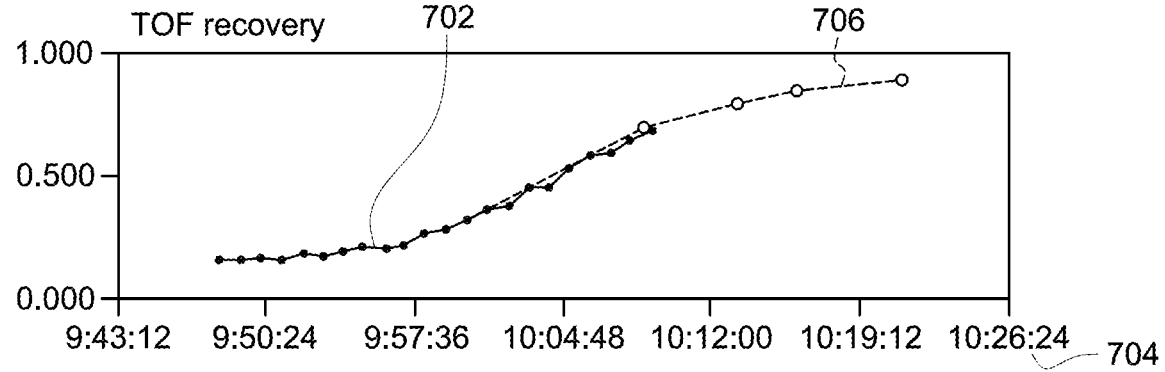
Figure 7E:
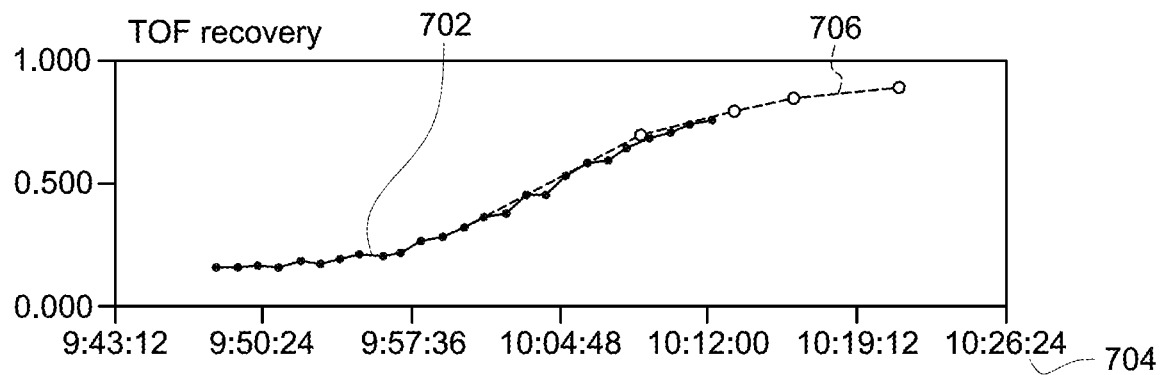
Figure 7F:
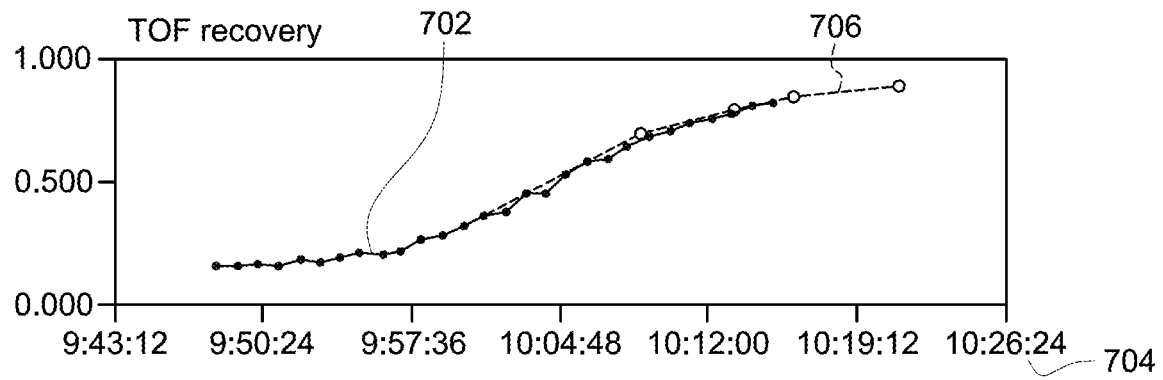
Figure 7G:
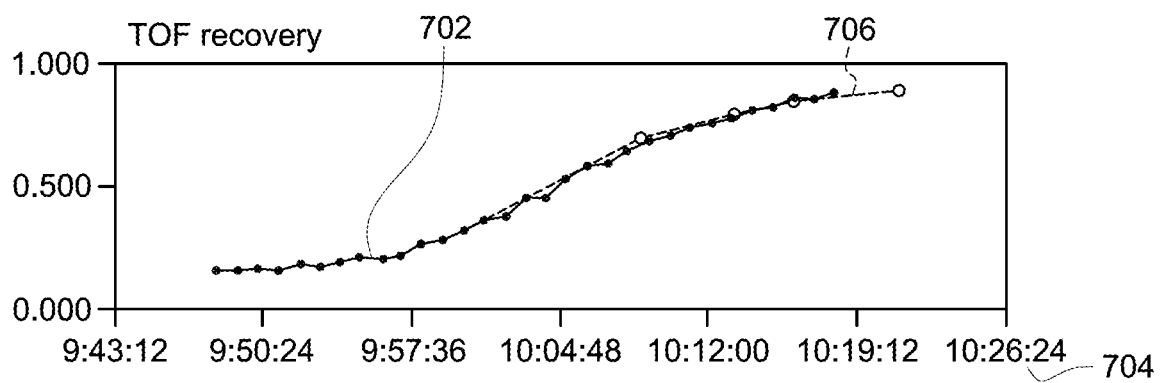
Figure 7H:
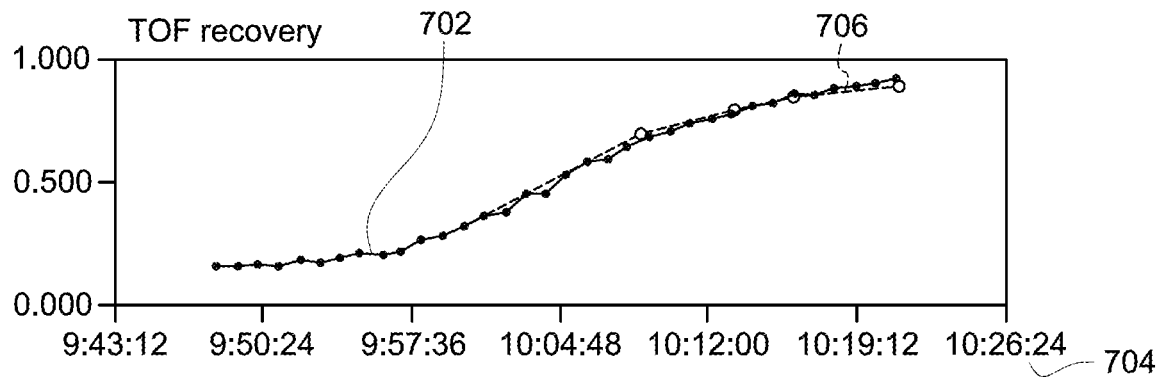

FIGS. 7A-7H several graphic displays taken over time based on clinical data. Each graphic display shows an estimated time of recovery calculated utilizing the system and method of the present disclosure. In FIG. 7A, a series of measured TOF ratios 702 are plotted along the time axis 704. As can be seen in FIG. 7A, the series of individual measured TOF ratios 702 begin to rise as the depth of relaxation lessens. In accordance with the present disclosure, a predicted neuromuscular blocking trend curve 706 is calculated and displayed along the time axis after the measured TOF ratios. In the embodiment shown in FIG. 7A, the estimated TOF will exceed 90% at the time of 10:21:16. This prediction was generated by the system at the time of 10:00:00. Thus, the clinician will have an estimated time of extubation approximately twenty-one minutes before the clinician would otherwise know this information if simply monitoring the changing measured values of the TOF ratio.

FIGS. 7B-7H illustrate further measurements 702 of the TOF ratio at later periods in time as plotted over the predicted neuromuscular blocking trend curve 706. As time passes, it can be seen in the graphs of FIG. 7 that the measured TOF ratios 702 closely match the predicted neuromuscular blocking trend curve 706 until FIG. 7H where the last measured TOF ratio 708 exceeds the recovery ratio threshold of 90%. In the embodiment illustrated, the estimated recovery time of 10:21:16, which was predicted at time 10:00:00 closely matched the actual time of 10:20:08 when the TOF ratio exceeded 90%. Thus, in the clinical data graphed and shown in FIG. 7, the method of the present disclosure was able to predict the estimated recovery time to a high degree of accuracy and provided this estimated recovery time to the clinician over twenty minutes before the TOF ratio reached the 90% threshold for extubation.

Figure 8:
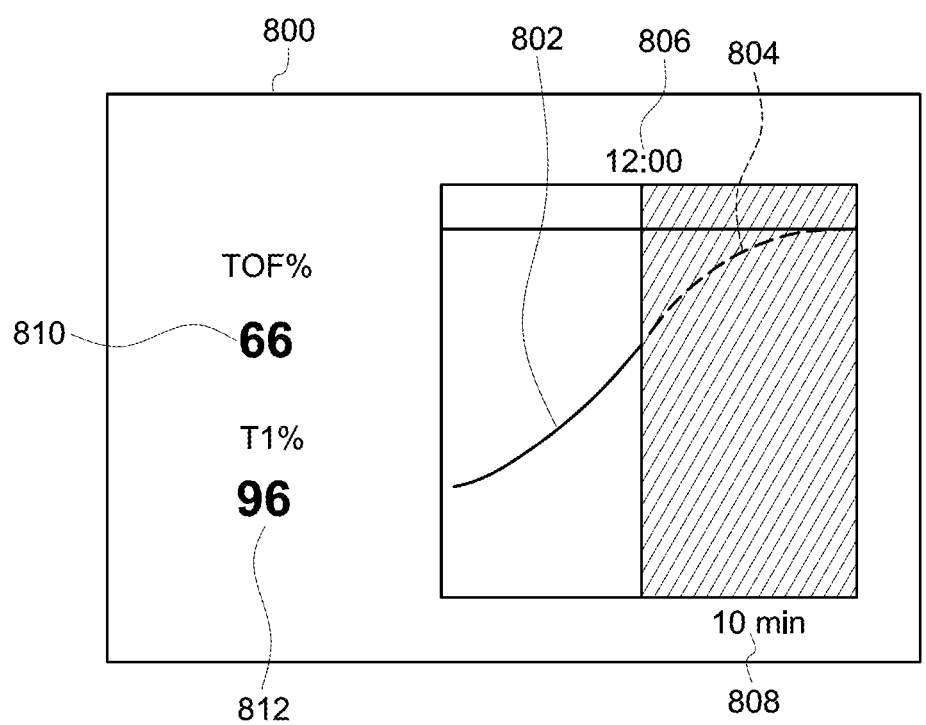
FIG. 8 is a display showing the estimated recovery time and predicted neuromuscular blocking trend curve.

FIG. 8 illustrates a display 800 that can be presented to the clinician utilizing the method and system of the present disclosure. The display 800 includes similar information as described above with reference to FIG. 7. Specifically, the measured TOF ratios 802 obtained from the patient are shown to the clinician relative to a vertical axis that represents the TOF ratio as a percentage and the horizontal time axis. In addition to the measured TOF ratios, the display 800 includes the predicted neuromuscular blocking trend curve 804 that is separated from the measured TOF trend by visually using different background and trend visualizations. The predicted neuromuscular blocking trend curve 804 is used to create an estimated recovery time that is shown to the clinician relative to the current time 806. Further, the display 800 includes the predicted recovery time 808 that provides the clinician with the amount of time that needs to run until extubation can occur. In this manner, the clinician is presented with an actual time 806 and the amount of time that needs to pass before extubation can occur. This information allows the clinician to make decisions as to whether to give an antidote, the type of antidote or to allow the patient to recover normally.

The display in FIG. 8 further includes a numeric illustration 810 of the present TOF ratio as well as the T1 percentage 812. The T1 percentage 812 is the ratio of the T1 muscle twitch relative to a reference value. The T1 percentage also provides an indication of how close the patient is to recovery that would allow extubation.

As discussed above, the method and system of the present disclosure creates a predicted neuromuscular blocking trend curve 804 shown in FIG. 8 that allows for a predicted time when the TOF ratio will exceed a threshold percentage and allow for safe extubation of the patient. The calculation of the predicted neuromuscular blocking trend curve can be done utilizing a wide variety of different algorithms that utilize not only measurements taken from the patient during TOF stimulation but also based upon data obtained from historical patient groups. Based upon data analysis and the study of recovery time, common trends and recovery graph shapes have been identified for patients in patient groups similar to the patient being monitored. The shape of the TOF trend curves determined over a large patient group can be utilized to generate the predicted neuromuscular blocking trend curve for the patient being monitored and thus implemented utilizing measured values from the actual patient.

In one contemplated example, before T4 responses and TOF ratios are available, train-of-two (TO2) ratios can be calculated for a patient. These TO2 ratios can then be utilized to calculate a slope of the TO2 trend. As the patient continues to recover, the calculated slope from the TO2 ratios can be applied to the measured TOF ratios from the patient and a predicted neuromuscular blocking trend curve is thus generated. Based upon this predicted neuromuscular blocking trend curve, an estimated recovery time is determined and shown to the clinician in a display similar to the display 800 shown in FIG. 8. Although this is one type of estimation method for predicting the estimated recovery time, various different methods and algorithms are contemplated as being within the scope of the present disclosure.

Figure 9:
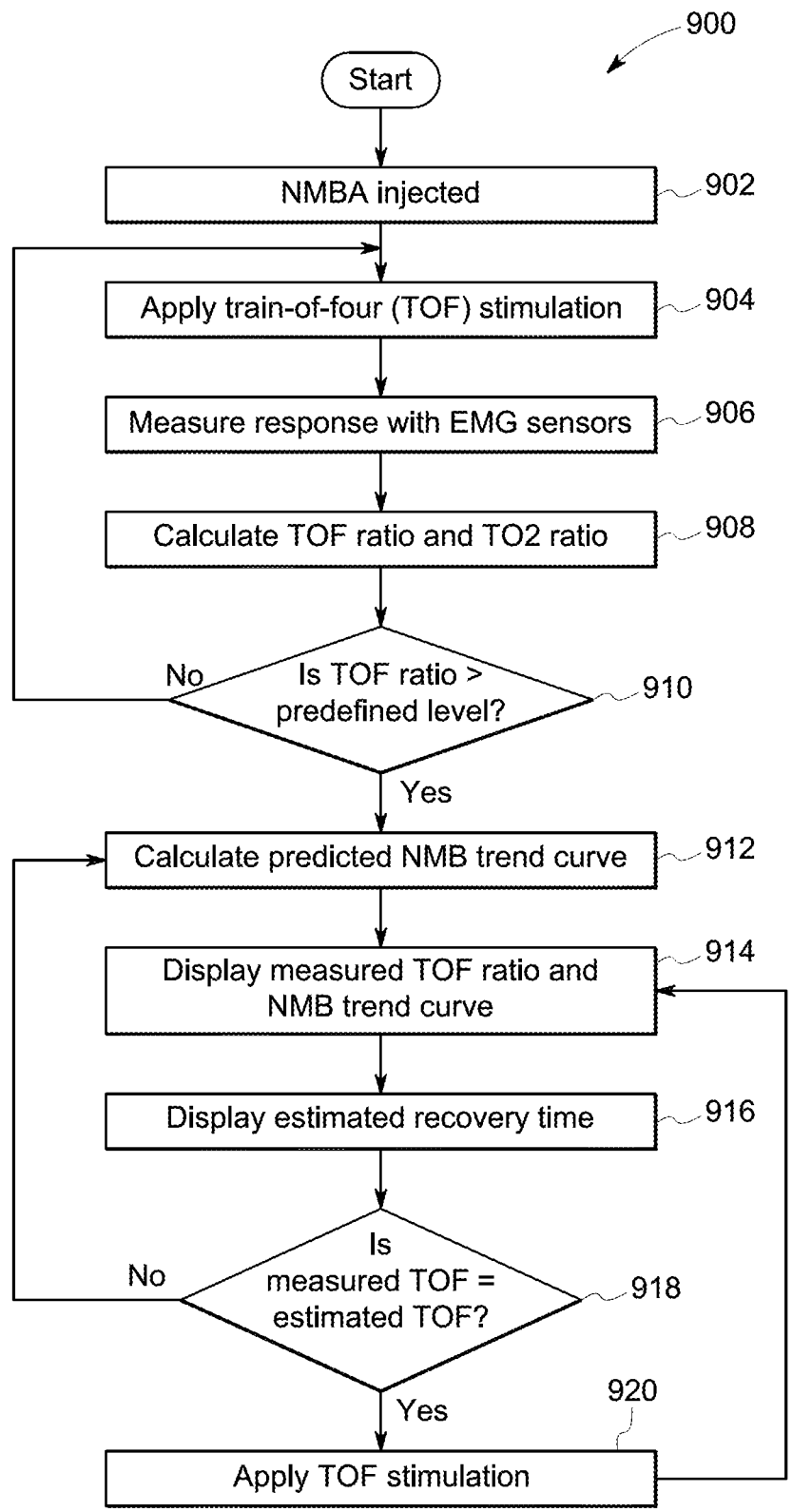
FIG. 9 is a flowchart illustrating one method of operating the system and method of the present disclosure.

FIG. 9 illustrates one method of operating the patient monitoring system in accordance with the present disclosure. As indicated in FIG. 9, the method begins with a neuromuscular blocking agent (NMBA) being injected in the patient in step 902. After the NMBA has been injected and begins to act, the patient needs to be continuously monitored during the surgical procedure.

At the end of the surgical procedure when the NMBA is being reduced and counteracted, the method begins to apply TOF stimulation to the patient in step 904. As described previously, TOF stimulation is one type of common monitoring used to determine depth of relaxation and to determine when a patient can be safely extubated. In step 906, the method measures the response of the patient to the TOF stimulation utilizing the EMG sensors 160 shown in FIG. 1. The application of the TOF stimulation in step 904 and the measurement of the responses in step 906 is a common procedure and generates the curves shown in FIG. 2. After the responses have been measured in step 906, the microcontroller of the neuromuscular transmission monitor 110 calculates standard values, such as the TOF ratio, the TO2 ratio and any other ratios that may be needed for monitoring the depth of relaxation.

Before the recovery time estimate is generated in accordance with the method of the present disclosure, the system determines in step 910 whether the TOF ratio exceeds a predefined level. The predefined level is used to determine when the patient initially begins to recover from the NMBA injected in step 902. The predefined level is the value that indicates that the patient has begun to recover and that the estimation calculation to be described below can begin. If the patient has not begun to recover, the system returns back to step 904 and the next TOF stimulation is applied. This process continues until the TOF ratio exceeds the predefined level in step 910 and the method then proceeds to step 912.

In step 912, the method calculates a predicted neuromuscular trend curve based upon the calculations made in step 908 and possibly based upon historic patient trend data. As discussed in previous portions of the present application, the predicted neuromuscular blocking trend curve calculated in step 912 can be calculated utilizing a variety of different types of algorithms and data analysis techniques. One possible algorithm and technique utilizes TO2 ratios calculated at multiple different points in time at which the TOF stimulation is applied to the patient. The TO2 ratios can be used to generate a slope and this slope can be used to extrapolate a predicted neuromuscular blocking trend curve for the TOF ratio. Such curves are shown in FIGS. 7 and 8 of the present disclosure.

Once the predicted NMB trend curve is calculated in step 912, the method moves to step 914 in which the measured TOF ratios and NMB trend curve are displayed, such as shown in FIG. 8. The display shown in FIG. 8 can also include an estimated recovery time, which is calculated and displayed in step 916. In this manner, the system and method of the present disclosure provides the clinician with not only the actual measured TOF ratios but also a predicted neuromuscular blocking trend curve in step 914 and an estimated time to recovery in step 916. Based upon all of this information, the clinician can then make treatment decisions, such as to administer an antidote, what type of antidote to administer or whether to allow the patient to recover under normal circumstances.

In step 918, the method and system can compare the most recent measured TOF ratio to an estimated TOF ratio which is based upon the predicted neuromuscular blocking trend curve. If the actual measured TOF ratio corresponds closely enough to the estimated TOF ratio for that time, the system proceeds to step 920 in which the next TOF stimulation is applied to the patient. This process continues as long as the patient remains intubated. Once the patient is extubated, the method and system shown in FIG. 9 can be terminated.

If the system determines in step 918 that the measured TOF ratio does not correspond closely enough to the estimated TOF ratio for that time, the system returns to step 912 where a new predicted NMB trend curve is calculated. In this manner, the system and method adjust the predicted neuromuscular blocking trend curve based upon measured values from the patient. In this manner, the system and method of the present disclosure is able to most accurately estimate recovery time and to present the most accurate estimated information to the clinician.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

I claim:

1. A method to estimate recovery time of a patient from neuromuscular block (NMB), comprising:
    applying a first series of stimulations including a first, a second, a third and a fourth stimulation, to a nerve of the patient at a first measurement time;
    measuring a first muscle twitch in response to the first stimulation and a second muscle twitch in response to the second stimulation in response to the first series of stimulations;
    calculating a first train-of-two (TO2) ratio based on the first muscle twitch and the second muscle twitch at the first measurement time;

applying a second series of stimulations including a first, a second, a third and a fourth stimulation, to the nerve of the patient at a second measurement time after the first measurement time;
measuring a first muscle twitch in response to the first stimulation and a second muscle twitch in response to the second stimulation in response to the second series of stimulations;
calculating a second train-of-two (TO2) ratio based on the first muscle twitch and the second muscle twitch at the second measurement time;
determining a predicted neuromuscular blocking trend curve based on the calculated first and second train-of-two (TO2) ratios;
utilizing a controller configured to determine a predicted neuromuscular blocking trend curve based on the calculated first and second train-of-two (TO2) ratios;
utilizing the controller also configured to estimate a recovery time based on the predicted blocking trend curve after the second measurement time; and
providing the estimated recovery time.

2. The method of claim 1 wherein the first series of stimulations and the second series of stimulations are train-of-four (TOF) stimulations.

3. The method of claim 2 wherein the first muscle twitch, the second muscle twitch, a third muscle twitch and a fourth muscle twitch are measured for each of the first and second TOF stimulations.

4. The method of claim 3 further comprising the steps of:
calculating a first train-of-four (TOF) ratio based on the first muscle twitch and the fourth muscle twitch at the first measurement time;
calculating a second train-of-four (TOF) ratio based on the first muscle twitch and the fourth muscle twitch at the second measurement time;
determining a predicted slope for the TOF ratio over time;
applying the predicted slope to the calculated first and second TOF ratios to create the predicted neuromuscular blocking trend curve; and
predicting the estimated recovery time based on the predicted neuromuscular blocking trend curve.

5. The method of claim 4 wherein the predicted neuromuscular blocking trend curve relates the TOF ratio to time.

6. The method of claim 5 wherein the predicted recovery time occurs when the TOF ratio of the predicted neuromuscular blocking trend curve exceeds a recovery threshold.

7. The method of claim 4 further comprising the step of displaying the predicted neuromuscular blocking trend curve.

8. The method of claim 4 wherein the displayed predicted neuromuscular blocking trend curve includes both measured and predicted TOF ratios.

9. The method of claim 1 further comprising the step of taking action to accelerate recovery time when the predicted recovery time exceeds a desired recovery time.

10. The method of claim 9 wherein the step of taking action includes delivering an antidote to the patient.

11. The method of claim 1 further comprising the step of outputting a notification instructing a user to initiate an extubation procedure at the estimate recovery time.

12. The method of claim 4 further comprising the steps of:
determining the TOF ratio at regular intervals after the second measurement time until the predicted recovery time;
comparing the determined TOF ratio to the TOF ratio of the predicted neuromuscular blocking trend curve for the measurement time; and
alerting a user when the determined TOF ratio differs from the predicted TOF ratio for the measurement time.

13. A method to estimate recovery time of a patient from neuromuscular block (NMB), comprising:
operating a stimulator to apply applying a first train-of-four (TOF) stimulation to a nerve of the patient at a first measurement time;
utilizing an electromyography (EMG) sensor to detect a first muscle twitch, a second muscle twitch, a third muscle twitch and a fourth muscle twitch in response to the first TOF stimulation;
calculating a first train-of-two (TO2) ratio based on the first muscle twitch and the second muscle twitch at the first measurement time; operating the stimulator to apply a second TOF stimulation to the nerve of a patient at a second measurement time;
utilizing the electromyography (EMG) sensor to detect a first muscle twitch, a second muscle twitch, a third muscle twitch and a fourth muscle twitch in response to the second TOF stimulation;
calculating a second TO2 ratio based on the first muscle twitch and the second muscle twitch at the second measurement time;
utilizing a controller configured to create a predicted neuromuscular blocking trend curve; and
utilizing a controller configured to predict the estimated recovery time based on the predicted neuromuscular blocking trend curve.

14. The method of claim 13 further comprising the step of displaying the predicted neuromuscular blocking trend curve on a display device.

15. The method of claim 14 wherein the displayed predicted neuromuscular blocking trend curve includes both measured and predicted TOF ratios.

16. The method of claim 13 further comprising the steps of:
calculating a first train-of-four (TOF) ratio based on the first muscle twitch and the fourth muscle twitch at the first measurement time;
calculating a second train-of-four (TOF) ratio based on the first muscle twitch and the fourth muscle twitch at the second measurement time;
applying the predicted slope to the calculated first and second TOF ratios to create the predicted neuromuscular blocking trend curve.

17. The method of claim 16 further comprising the steps of:
determining the TOF ratio at regular intervals after the second measurement time until the predicted recovery time at regular intervals;
comparing the determined TOF ratio to the TOF ratio of the predicted neuromuscular blocking trend curve for the measurement time; and
alerting a user when the determined TOF ratio differs from the predicted TOF ratio for the measurement time.

18. A medical device for monitoring depth of relaxation of a patient, comprising:
a stimulator configured to apply train-of-four (TOF) stimulation to a nerve of the patient at first and second measurement times;
an electromyography (EMG) sensor configured to detect a first muscle twitch, a second muscle twitch, a third muscle twitch and a fourth muscle twitch in response to the TOF stimulation at the first and second measurement times;
a controller configured to create a predicted neuromuscular blocking trend curve based on train-of-two (TO2)

ratios calculated based on the detected first and second muscle twitches at the first and second measurement times, wherein the predicted neuromuscular blocking trend curve indicates a predicted extubation time.

19. The medical device of claim 18 further comprising a display for visually displaying the predicted neuromuscular blocking trend curve.

20. The medical device of claim 19 wherein the predicted neuromuscular blocking trend curve included measured TOF ratios and predicted TOF ratios.

* * * * *